(12) United States Patent
Wacher et al.

(10) Patent No.: US 6,180,666 B1
(45) Date of Patent: *Jan. 30, 2001

(54) USE OF GALLIC ACID ESTERS TO INCREASE BIOAVAILABILITY OF ORALLY ADMINISTERED PHARMACEUTICAL COMPOUNDS

(75) Inventors: Vincent J. Wacher, San Francisco; Leslie Z. Benet, Belvedere, both of CA (US)

(73) Assignee: AnMax, Inc., So. San Francisco, CA (US)

(*) Notice: Under 35 U.S.C. 154(b), the term of this patent shall be extended for 0 days.

This patent is subject to a terminal disclaimer.

(21) Appl. No.: 09/264,215

(22) Filed: Mar. 5, 1999

Related U.S. Application Data

(63) Continuation-in-part of application No. 08/926,309, filed on Sep. 5, 1997, now Pat. No. 5,962,522.

(51) Int. Cl.[7] ....................... A61K 31/235; A61K 31/353

(52) U.S. Cl. ..................... 514/544; 514/456; 514/457

(58) Field of Search .................................. 514/544, 456, 514/457

(56) References Cited

U.S. PATENT DOCUMENTS

| | | | |
|---|---|---|---|
| 3,282,789 | 11/1966 | Bernard et al. | 167/82 |
| 4,310,543 | 1/1982 | Gallo-Torres et al. | 424/305 |
| 4,716,173 | 12/1987 | Salantinjants | 514/314 |
| 5,156,842 | 10/1992 | Mulligan | 424/195.1 |
| 5,567,592 | 10/1996 | Benet et al. | 435/7.21 |
| 5,665,386 | 9/1997 | Benet et al. | 424/451 |

FOREIGN PATENT DOCUMENTS

| | | |
|---|---|---|
| 0 184 942 A2 | 6/1986 | (EP). |
| 0 295 941 B1 | 12/1988 | (EP). |
| 0 314 384 A2 | 5/1989 | (EP). |
| 997914 | 7/1965 | (GB). |
| 9520980 | 8/1995 | (WO). |
| WO 96/01128 | 1/1996 | (WO). |
| WO 96/40192 | 12/1996 | (WO). |

OTHER PUBLICATIONS

Apostolides, Z., et al., "Inhibition of PhIP mutagenicity by catechins, and by theaflavins and gallate esters," *Mutation Research*, 389(2–3):167–172 (1997).

Baer–Dubowska, W., et al., "Inhibition of murine hepatic cytochrome P450 activities by natural and synthetic phenolic compounds," *Xenobiotica*, 28(8):735–43 (1998).

Bamforth, K.J., et al., "Common food additives are potent inhibitors of human liver 17α–ethinyloestradiol and dopamine sulphotransferases," *Biochem. Pharmacol.*, 46(10):1713–1720 (1993).

Bonkovsky et al., "Cytochrome $P_{450}$ of Small Intestinal Epithelial Cells," *Gastroenterology*, 88:458–467 (1985).

Bourrié, M., et al., "Cytochrome P450 Isoform Inhibitors as a Tool for the Investigation of Metabolic Reactions Catalyzed by Human Liver Microsomes," *J. Pharmacol. Exp. Ther.*, 277(1):321–332 (1996).

Bradford, M.M., "A rapid and sensitive method for the quantitation of microgram quantities of protein utilizing the principles of protein–dye binding," *Anal. Biochem.*, 72:248–254 (1976).

Burke, M. D., et al., "Ethoxy–, Pentoxy and Benzyloxyphenoxazones and Homologues: A Series Of Substrates To Distinguish Between Different Induced Cytochromes P–450," *Biochem. Pharmacol.*, 34(18):337–3345 (1985).

Clarke, S.E., et al., "Characterization of the inhibition of P4501A2 by furafylline," *Xenobiotica*, 24:517–26 (1994).

Fabre, G., et al., "Evidence of CYP3A–mediated N–deethylation of amiodarone in human liver microsomal fractions," *Drug Metab. Dispos.*, 21(6):978–985 (1993).

Fasco et al., "Rat Small Intestinal Cytochromes P450 Probed by Warfarin Metabolism," *Mol. Pharmacol.*, 43:226–233 (1993).

Gonzalez, F.J., et al., "Human P450PCN1: Sequence, Chromosome Localization, and Direct Evidence through cDNA Expression That P450PCN1 Is Nifedipine Oxidase, *DNA*," 7(2):79–86 (1988).

Greenblatt, David J., "Presystemic Extraction: Mechanisms and Consequences," *J. Clin. Pharmacol.*, 33:650–656 (1993).

Kaminsky et al., "Small Intestinal Cytochromes P450," *Toxicology*, 21(6):407–422 (1992).

Kedderis, G.L., et al., "Characterization of the N–Demethylation Reactions Catalyzed by Chloroperoxidase," *Microsomes, Drug Oxic., Chem. Carcinoq.*, Int. Symp. Microsomes Drug Oxid., 1:351–4, pub. Academic Press, eds. Coon, et al. (1980).

Kedderis, G.L., et al., "N–Demethylation Reactions Catalyzed by Chloroperoxidase," *J. Biol. Chem.*, 255(21):10174–82 (1980).

Kelleher, J., et al., "Modification of Paracetamol Hepatotoxicity by Anti–Oxidants," *J. Ind. Med. Res.*, 4 suppl. (4):138–144 (1976).

Kelleher, J., et al., "Modifications of Paracetamol Toxicity by Antioxidants," *Biochem. Soc. Transact.*, 4:292–294 (1976).

(List continued on next page.)

Primary Examiner—Phyllis G. Spivack
(74) *Attorney, Agent, or Firm*—Cooley Godward LLP

(57) ABSTRACT

A method is disclosed for increasing bioavailability of an orally administered pharmaceutical compound comprising orally coadministering the pharmaceutical compound to a mammal in need of treatment with the compound and a gallic acid ester. Preferred gallic acid esters of the invention include octyl gallate, propyl gallate, lauryl gallate, and methyl gallate. Improved formulations of pharmaceutical compounds include the gallic acid ester to enhance the bioavailability of the active ingredient of the pharmaceutical compound.

54 Claims, No Drawings

OTHER PUBLICATIONS

Kivistö, K.T., et al., "Plasma buspirone concentrations are greatly increased by erythromycin and itraconazole," *Clin. Pharmacol. Ther.,* 62(3):348–354 (1997).

Kolars, J.C. et al., "Identification of Rifampin–Inducible P450III A4 (CYP3A4) in Human Small Bowel Enterocytes," *J. Clin. Investig.,* 90:1871–1878 (1992).

Kolars et al., "Heterogeneity of Cytochrome P450IIIA Expression in Rat Gut Epithelia," *Gastroenterology,* 102:1188–1198 (1992).

Komori et al., "Cytochrome P–450 in Human Liver Microsomes: High–Performance Liquid Chromatographic Isolation of Three Forms and Their Characterization," *J. Biochem.,* 104:912–16 (1988).

Kronbach et al., "Cyclosporine Metabolism in Human Liver: Identification of a Cytochrome P–450III Gene Family as the Major Cyclosporine–Metabolizing Enzyme Explains Interactions of Cyclosprine with Other Drugs," *Clin. Pharmacol. Ther.,* 43(6):630–5 (1988).

Leemann, T., et al., "Cytochrome P450TB (CYP2C): A Major Monooxygenase Catalyzing Diclofenac 4'-Hydroxylation in Human Liver," *Life Sciences,* 52:29–34 (1992).

Lilja, J.J., et al., "Grapefruit juice substantially increases plasma concentrations of buspirone," *Clin. Pharmacol. Ther.,* 64(6);655–660 (1998).

Lown, K.S., et al., "Sequences of Intestinal and Hepatic Cytochrome P450 3A4 cDNAs are Identical," *Drug Metab. Dispos.,* 26(2):185–187 (1998).

Lucas, D., et al., "Chlorzoxazone: An in Vitro and in Vivo Substrate Probe for Liver CYP2E1," *Methods in Enzymology,* 272:115–123 (1996).

Miller, C. et al., "Modulation of the mutagenicity and metabolism of the tobacco-specific nitrosamine 4–(methylnitrosamino)–1–3(3–pyridyl)–1–butanone (NNK) by phenolic compounds," *Mutation Research,* 368(3–4)221–233 (1996).

Nash, "The Colorimetic Estimation of Formaldehyde by Means of the Hantzach Reaction," *Biochem. J.,* 55:416–421 (1953).

Nelson, D. R., et al., "P450 superfamily: update on new sequences, gene mapping, accession numbers and nomenclature," *Pharmacogenetics,* 6:1–42 (1996).

Newton, D.J., et al., "Cytochrome P450 Inhibitors: Evaluation of Specificities in the In Vitro Metabolism of Therapeutic Agents by Human Liver Microsomes," *Drug Metabolism and Disposition,* 23(1):154–158 (1995).

Omura, T., et al., "The Carbon Monoxide–Binding Pigment of Liver Microsomes II. Solubilization, Purification and Properties," *J. Biol. Chem.,* 239:2370–2378 (1964).

Schmiedlin–Ren et al., "Cultured Adult Rat Jejunal Explants as a Model for Studying Regulation of CYP3A," *Biochem. Pharmacol.,* 46(5):905–918 (1993).

Somberg et al., "The Clinical Implications of First–Pass Metabolism: Treatment Strategies for the 1990's," *J. Clin. Pharmacol.,* 33:670–673 (1993).

Straehl, P., et al., "Isosorbide 5–Mononitrate and Isosorbide 2–Mononitrate Kinetics after Intravenous and Oral Dosing," *Clin. Pharmacol. Ther.,* 36(4):485–492 (1985).

Straehl, P., et al., "Isosorbide Dinitrate Bioavailability, Kinetics, and Metabolism," *Clin. Pharmacol. Ther.,* 38(2):140–149 (1985).

Stuckey, Ben N., "Antioxidants as Food Stabilizers," *CRC Handbook of Food Additives,* 2$^{nd}$ ed., pp. 185–199 (1980).

Tam, Yun K., "Individual Variation in First–Pass Metabolism," *Clin. Pharmacokinet,* 25(4):300–328 (1993).

Trivier et al., "Amiodarone N–deethylation in human liver microsomes: involvement of cytochrome P450 3A enzymes (first report)," *Life Sci.,* 52:PL91–96 (1993).

van Hoogdalem et al., "Intestinal Drug Absorbtion Enhancement: An Overview," *Pharmacol. Ther.,* 44:407–443 (1989).

Wacher, V. J., et al., "Role of P–Glycoprotein and Cytochrome P450 3A in Limiting Oral Absorption of Peptides and Peptidomimetics," *Journal of Pharmaceutical Sciences* 87(11):1322–1330(1998).

Watkins et al., "Identification of Glucocorticoid–Inducible Cytochromes P–450 in the Intestinal Mucosa of Rats and Man," *J. Clin. Invest.,* 80:1029–36 (1987).

Watkins et al., "The Role of Cytochromes P450 in Cyclosporine Metabolism," *J. Am. Acad. Dermacol.,* 23:1301–1309 (1990).

Watkins et al., "Drug Metabolism by Cytochromes P450 in the Liver and Small Bowel," *Gastrointestinal Pharmacology,* 21(3):511–527 (1992).

Weinke, S., et al., "Effect of four synthetic antioxidants on the formations of ethylene from methional in rat liver microsomes," *Toxicology Letters,* 35:247–251 (1987).

WHO Food Additives Series, vol. 32:3–23 (1993), Abstract.

World Health Organization, "Evaluation of certain food additives and contaminants," Pamphlet #837, pp.6–7, Geneva (1993).

Wrighton et al., "Demonstration in Multiple Species of Inducible Hepatic Cytochromes P–450 and their mRNAs Related to the Glucocorticoid–Inducible Cytochrome P–450 of the Rat," *Molecular Pharmacology,* 28:312–321 (1985).

Wrighton et al., "Studies on the Expression and Metabolic Capabilities of Human Liver Cytochrome P450IIIA5 (HLp3)," *Mol. Pharmacol.,* 38:207–213 (1990).

Wu et al., "Use of IV and Oral Drug Levels from Cyclosporine (CsA) with Concomitant Rifampin to Differentiate Gut Absorption and Metabolism," *Pharm. Res.* 10; Abstract #PPDM 8185 (1993).

Yang et al., "Inhibitions of Hepatic Mixed Function Oxidase Activity by Propyl Gallate," *Biochem. Pharmacol.,* 23:3129–3138 (1974).

Abstract for Japanese Patent No. JP 0220 2813 A JP, (Aug. 28, 1993).

Abstract for Japanese Patent No. JP 0220 2813 A2, (Aug. 10, 1990).

Obermeier et al., "Effects of Bioflavonoids on Hepatic P450 Activities," *Xenobiotica,* 25(6):575–584, (1995).

Wang et al., "Interaction of Epicatechins Derived from Green Tea with Rat Hepatic Cytochrome P–450," *Drug Metabolism and Disposition,* 16(1):98–103, (1988).

USE OF GALLIC ACID ESTERS TO INCREASE BIOAVAILABILITY OF ORALLY ADMINISTERED PHARMACEUTICAL COMPOUNDS

CROSS-REFERENCE TO RELATED APPLICATIONS

This application is a continuation-in-part of application U.S. Ser. No. 08/926,309, filed Sep. 5, 1997, now U.S. Pat. No. 5,962,522.

INTRODUCTION

Technical Field

This invention is directed to the field of pharmacology and particularly to the formulation of oral pharmaceutical compositions for increased bioavailability and reduced inter- and intra-individual variability.

Background

Pharmacokinetics is the study of the fate of pharmaceuticals from the time they are ingested until they are eliminated from the body. The sequence of events for an oral composition includes absorption through the various mucosal surfaces, distribution via the blood stream to various tissues, biotransformation in the liver and other tissues, action at the target site, and elimination of drug or metabolites in urine or bile.

Bioavailability of a drug (pharmaceutical composition) following oral dosing is a critical pharmacokinetic determinant which can be approximated by the following formula:

$$F_{oral} = F_{ABS} \times F_G \times F_H$$

where $F_{oral}$ is the oral bioavailability fraction, which is the fraction of the oral dose that reaches the circulation in an active, unchanged form. $F_{oral}$ is less than 100% of the active ingredient in the oral dose for four reasons: (1) drug is not absorbed out of the gut lumen into the cells of the intestine and is eliminated in the feces; (2) drug is absorbed into the cells of the intestine but back-transported into the gut lumen; (3) drug is biotransformed by the cells of the intestine (to an inactive metabolite); or (4) drug is eliminated by the cells of the liver, either by biotransformation and/or by transport into the bile. Thus, oral bioavailability is the product of the fraction of the oral dose that is absorbed ($F_{ABS}$), the fraction of the absorbed dose that successfully reaches the blood side of the gastrointestinal tract ($F_G$), and the fraction of the drug in the GI blood supply that reaches the heart side of the liver ($F_H$). The extent of gut wall absorption, back transport and metabolism, and liver elimination are all subject to wide inter- and intra-individual variability.

Previous investigations arising in the laboratory of one of the present inventors resulted in new understandings of factors involved with bioavailability and in the invention described in U.S. Pat. No. 5,567,592. The '592 patent describes general methods for increasing bioavailability of oral pharmaceutical compositions and methods for identifying compounds that increase bioavailability. However, although that invention made it possible to investigate a number of classes of compounds not previously thought to be useful in enhancing bioavailability, the actual process of identifying specific classes of compounds that are superior bioenhancers, among those bioenhancers which work to some degree, still remains a process of investigation and discovery. For example, the use of essential oils to enhance bioavailability of an orally administered pharmaceutical composition is disclosed in U.S. Pat. No. 5,665,386.

SUMMARY OF THE INVENTION

An object of this invention is to identify compositions with superior ability to increase drug bioavailability, particularly by increasing net drug absorption and/or decreasing drug biotransformation in the gut wall by inhibiting cytochrome P450 drug metabolism.

Another object of the invention is to provide compositions that strongly inhibit enzymes of the cytochrome P450 3A class (CYP3A) in the gut in preference to in other locations, such as the liver, which was previously thought to be the primary site of drug metabolism.

One specific object of the present invention is to reduce inter-individual variability of the systemic concentrations of the active pharmaceutical compound, as well as intra-individual variability of the systemic concentrations of the pharmaceutical compound being administered.

The invention is carried out by co-administering a gallic acid ester with an oral pharmaceutical compound (drug) or compounds to increase drug bioavailability. Particularly preferred esters are octyl gallate, propyl gallate, lauryl gallate, and methyl gallate. The compositions and methods of the invention can be used to increase drug efficacy in humans and in other mammals. Although veterinary use is specifically contemplated, the primary use will be in human treatment. Administration schemes include, but are not limited to, use of oral and topical formulations in humans and use of similar formulations for livestock.

DESCRIPTION OF SPECIFIC EMBODIMENTS

Gallic Acid Esters Increase Drug Bioavailability

The present invention arises from continued research into the factors affecting drug bioavailability that were described in earlier applications arising from the laboratory of one of the present inventors. "Drug bioavailability" is defined here as the total amount of drug systemically available over time. The present invention provides a method for increasing drug bioavailability by inhibiting drug biotransformation in the gut using one or more of the compounds described herein. The compound(s) responsible for increased drug bioavailability is a gallic acid ester. The present inventors have discovered that gallic acid esters, in general, are capable of inhibiting the enzyme(s) responsible for drug biotransformation in the gut.

In general, the present invention provides a method for increasing the bioavailability of an orally administered pharmaceutical compound (particularly one which is hydrophobic) by orally co-administering the pharmaceutical compound to a mammal in need of treatment with an amount of a gallic acid ester sufficient to provide integrated systemic concentrations over time of the pharmaceutical compound greater than the integrated systemic concentrations over time of the pharmaceutical compound in the absence of the gallic acid ester. At least one gallic acid ester is utilized in the method of the invention to increase bioavailability. However, two or more gallic acid esters may be used simultaneously in the practice of the invention, leading to further increased bioavailability of the pharmaceutical compound, depending on the particulars of the compound. Changes in the integrated systemic concentrations over time are indicated by "area under the curve" (AUC) measurements, an accepted pharmacological technique described in detail below.

Gallic acid esters

Gallic acid esters useful in the present invention have the general formula shown below:

(Formula I)

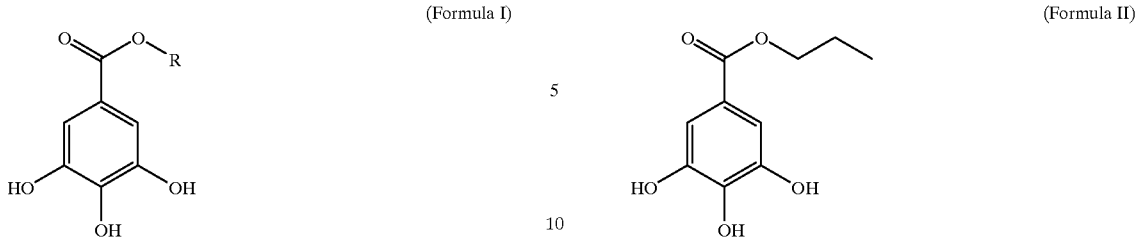

(Formula II)

The R group may be an alkyl, alkenyl, alkynyl, aryl, benzyl, phenyl, alicyclic, or heterocyclic group, all of which groups may be substituted or unsubstituted. R is preferably a $C_1$–$C_{22}$ alkyl group, a $C_2$–$C_{22}$ alkenyl group or a $C_2$–$C_{22}$ alkynyl group, all of which groups may be substituted or unsubstituted and may be straight chain or branched chain. R is more preferably a $C_1$–$C_{12}$ alkyl group, particularly a methyl, propyl, octyl or dodecyl (lauryl) group, or a $C_2$–$C_{19}$ alkenyl group, particularly a cis-9-hexadecenyl (palmitoleyl), cis-9-octadecenyl (oleyl), cis,cis-9,12-octadecadienyl (linoleyl), trans,trans-9,12-octadecadienyl (linolelaidyl), cis,cis,cis-9,12,15-octadecatrienyl (linolenyl), trans,transtrans-9,12,15-octadecatrienyl (linolenelaidyl), cis,cis,cis-6,9,12-octadecatrienyl (gamma-linolenyl), trans-9-octadecenyl (elaidyl) or trans-9-hexadecenyl (palmitelaidyl) group.

Many of the gallic acid esters used in the practice of the present invention are commercially available compounds or may be readily synthesized by methods that are well known in the art, for example, by refluxing gallic acid and the appropriate alcohol (R-OH) in the presence of acid using standard conditions as described in Vogel, A., *Vogel's Textbook of Organic Chemistry*, 4$^{th}$ Edition, revised by Furniss, B. S. et al., Longman Inc., N.Y. (1978).

In a recently published example, lauryl gallate was prepared in greater than 90% yield by refluxing gallic acid and lauryl alcohol in dioxane in the presence of p-toluenesulfonic acid and zeolite (Chen, L. and Wu, K., New process of synthesis of lauryl gallate, *Huaxue Shiji* 19:382 (1997).

The gallic acid ester is preferably presented for coadministration in a ratio of gallic acid ester to drug in the range of 0.01 to 100 units gallic acid ester to 1 unit of the drug. For example, a formulation having 1 mg gallic acid ester per 100 mg drug represents the lower end of this range and a formulation having 500 mg gallic acid ester per 5 mg drug represents the upper end of this range. A more preferred range of gallic acid ester to drug in accordance with the present invention is 0.1 to 10 units gallic acid ester to 1 unit of the drug. The most preferred range is 0.5 to 2 units gallic acid ester 1 unit of the drug.

Properties of Gallic Acid Esters

The structure of propyl gallate (3,4,5-trihydroxybenzoic acid, n-propyl ester) is shown below:

Propyl gallate has been used as an antioxidant or preservative in foods, drugs, cosmetics and pesticide products since 1948. This compound is Generally Recognized As Safe (GRAS) by the FDA and is listed in the Everything Added to Food in the United States (EAFUS) database as well as the United States Pharmacopeia-National Formulary (USP-NF) and the Food Chemicals Codex. The Joint Food and Agricultural Organization/World Health Organization Expert Committee on Food Additives has established an acceptable daily intake of 0–1.4 mg/kg/day for this compound. This value is $\frac{1}{100}$ of the "no observed effect" level determined in a 90 day feeding study in rats ("Gallates: Propyl, Octyl, Dodecyl," *WHO Food Additive Series,* 32:3–23 (1993)).

Octyl gallate and lauryl gallate have also been used as antioxidants in food; however, their current use is limited. The Joint Food and Agriculture Organization/World Health Organization Expert Committee on Food Additives has established temporary acceptable daily intake levels of 0–0.1 mg/kg body weight for octyl gallate and 0–0.05 mg/kg body weight for lauryl gallate. These values are $\frac{1}{200}$ of the "no observed effect level" determined in 90 day feeding studies in rats ("Gallates: Propyl, octyl, dodecyl." *WHO Food Additive Series* 32: 3–23 (1993); Forty-first Report of the Joint FAO/WHO Expert Committee on Food Additives. Evaluation of certain food additives and contaminants. *WHO Technical Report Series* 837:6, 46 (1993)). Lauryl gallate and octyl gallate are listed in the Everything Added to Food in the US (EAFUS) database, but neither of these compounds is listed in the United States Pharmacopeia-National Formulary (USP-NF) or the Food Chemical Codex.

Because these three alkyl gallate esters in very low concentrations, as have been used previously for the antioxidant purposes discussed above, are of low activity and thus not likely to be useful for the purposes described generally herein, only concentrations of a gallic acid ester providing an inhibition activity (resulting in increased bioavailability of a co-administered drug) are included in the invention. Preferred are those formulations of a gallic acid ester that show an inhibition of at least 20% at a 1:1 gallic acid ester:drug ratio; even more preferred are formulations of a gallic acid ester that show an inhibition of at least 50% at the same gallic acid ester to drug ratio.

Bioavailability Measurements

The increase in drug bioavailability attributable to administration of the gallic acid ester can be determined by measuring total systemic drug concentrations over time after coadministration of a drug and the gallic acid ester and after administration of only the drug. The increase in drug bioavailability is defined as an increase in the Area Under the Curve (AUC). AUC is the integrated measure of systemic drug concentrations over time in units of mass-time/volume. The AUC from time zero (the time of dosing) to time infinity (when no drug remains in the body) following the administration of a drug dose is a measure of the exposure of the patient to the drug. When efficacy of the gallic acid ester is being measured, the amount and form of active drug administered should be the same in both the coadministration of drug and gallic acid ester and the administration of the drug alone. For instance, administration of 10 mg of drug alone may result in total systemic drug delivered over time (as measured by AUC) of 500 μg•hr/ml. In coadministration (i.e., in the presence of the gallic acid ester) the systemic drug AUC may increase to 700 μg•hr/ml. If significantly increased drug bioavailability in the presence of the gallic acid ester is anticipated, drug doses may need to be reduced for safety.

Systemic drug concentrations are measured using standard drug measurement techniques. "Systemic drug concentration" refers to a drug concentration in a mammal's bodily fluids, such as serum, plasma or blood; the term also includes drug concentrations in tissues bathed by the systemic fluids, including the skin. Systemic drug concentration does not refer to digestive fluids. The increase in total systemic drug concentrations is one way of defining an increase of drug bioavailability due to coadministration of gallic acid ester and the drug. For drugs excreted in part unmetabolized in the urine, an increased amount of unchanged drug in the urine will reflect the increase in systemic concentrations.

Characteristics of Drugs Used with Gallic Acid Esters

The word "drug" as used herein is defined as a chemical capable of administration to an organism which modifies or alters the organism's physiology. More preferably the word "drug" as used herein is defined as any substance intended for use in the treatment or prevention of disease. Drug includes synthetic and naturally occurring toxins and bioaffecting substances as well as recognized pharmaceuticals, such as those listed in "The Physicians Desk Reference," 49th edition, 1995, pages 101–338; "Goodman and Gilman's The Pharmacological Basis of Therapeutics" 9th Edition (1996), pages 103–1645 and 1707–1792; and "The United States Pharmacopeia, The National Formulary," USP 23 NF 18 (1995), the compounds of these references being herein incorporated by reference. The term drug also includes compounds that have the indicated properties that are not yet discovered or available in the U.S. The term drug includes pro-active, activated and metabolized forms of drugs. The present invention can be used with drugs consisting of charged, uncharged, hydrophilic, zwitter-ionic, or hydrophobic species, as well as any combination of these physical characteristics. A hydrophobic drug is defined as a drug which in its non-ionized form is more soluble in lipid or fat than in water. A preferred class of hydrophobic drugs is those drugs more soluble in octanol than in water.

In the method of the present invention, compounds (or drugs) from a number of classes of compounds that can be administered with gallic acid esters include, for example, the following classes: acetanilides, anilides, aminoquinolines, benzhydryl compounds, benzodiazepines, benzofurans, cannabinoids, cyclic peptides, dibenzazepines, digitalis gylcosides, ergot alkaloids, flavonoids, imidazoles, quinolines, macrolides, naphthalenes, opiates (or morphinans), oxazines, oxazoles, phenylalkylamines, piperidines, polycyclic aromatic hydrocarbons, pyrrolidines, pyrrolidinones, stilbenes, sulfonylureas, sulfones, triazoles, tropanes, and vinca alkaloids.

Increased Drug Bioavailability by Inhibition of Cytochrome P450

Phase I Biotransformation

Inhibition of enterocyte cytochromes P450 participating in drug biotransformation is one objective of the present invention. The major enzymes involved in drug metabolism are present in the endoplasmic reticulum of many types of cells but are at the highest concentration in hepatocytes. Traditionally, enterocyte biotransformation was considered of minor importance in biotransformation compared to the liver. Many compounds inhibit cytochrome P450. These include, but are not limited to, ketoconazole, troleandomycin, gestodene, flavones such as quercetin and naringenin, erythromycin, ethynyl estradiol, and prednisolone. The primary goal of the invention is to use gallic acid ester to inhibit drug cytochrome P450 biotransformation in the gut to increase drug bioavailability.

Types of Cytochromes and Tissue Location

The cytochromes P450 are members of a superfamily of hemoproteins. They represent the terminal oxidases of the mixed function oxidase system. The cytochrome P450 gene superfamily is composed of at least 207 genes that have been named based on their evolutionary relationships. For this nomenclature system, the sequences of all of the cytochrome P450 genes are compared, and those cytochromes P450 that share at least 40% identity are defined as a family (designated by CYP followed by a Roman or Arabic numeral, e.g. CYP3), further divided into subfamilies (designated by a capital letter, e.g. CYP3A), which are comprised of those forms that are at least 55% related by their deduced amino acid sequences (Nelson et al., P450 superfamily: update on new sequences, gene mapping accession numbers and nomenclature, *Pharmacogenetics* 6:1–42 (1996)). Finally, the gene for each individual form of cytochrome P450 is assigned an Arabic number (e.g. CYP3A4).

Three cytochrome P450 gene families (CYP1, CYP2 and CYP3) appear to be responsible for most drug metabolism. At least 15 cytochromes P450 have been characterized to varying degrees in the human liver. At concentrations of the substrates found under physiologic conditions, enzyme kinetics often favor a single form of cytochrome P450 as the primary catalyst of the metabolism of a particular drug or other enzyme substrate.

The CYP3 gene family encoding cytochromes P450 of type 3 is possibly the most important family in human drug metabolism. At least 5 forms of cytochrome P450 are found in the human 3A subfamily, and these forms are responsible for the metabolism of a large number of structurally diverse drugs. In non-induced individuals, 3A may constitute 20% of the P450 enzymes in the liver. In enterocytes, members of the 3A subfamily constitute greater than 70% of the cytochrome-containing enzymes. The present inventors have discovered that gallic acid esters preferentially inhibit the CYP3A form over the enzymes from the CYP1 and CYP2 families. The first two human 3A subfamily members identified were 3A3 and 3A4. These two cytochromes P450 are so closely related that the majority of studies performed to date have not been able to distinguish their contributions, and thus they are often referred to as 3A3/4. Erythromycin N-demethylation, cyclosporine oxidation, nifedipine oxidation, midazolam hydroxylation, testosterone 6β-hydroxylation, and cortisol 6β-hydroxylation are all in vitro probes of 3A3/4 catalytic activity. The levels of 3A3/4 vary by as much as 60-fold between human liver microsomal samples, with the levels of 3A forms approaching 50% of the total cytochrome P450 present in human liver samples from individuals receiving inducers of 3A3/4. The recently studied CYP3A5 may also play a role as important as 3A3/4.

The liver contains many isoforms of cytochrome P450 and can biotransform a large variety of substances. The enterocytes lining the lumen of the intestine also have significant cytochrome P450 activity, and this activity is dominated by a single family of isozymes, 3A, the most important isoforms in drug metabolism.

Increased Drug Efficacy by Reducing CYP3A Drug Biotransformation

The gallic acid ester, as used according to the invention, reduces drug biotransformation in the gut by inhibiting CYP3A activity in gut epithelial cells which leads to a total increase in drug bioavailability in the serum. In the presence of the gallic acid ester, fewer drug molecules will be metabolized by phase I enzymes in the gut and will not be available for phase II conjugation enzymes. This will lead to increased concentrations of untransformed drug passing from the gut into the blood and onto other tissues in the body.

Although the primary objective of the gallic acid ester is to inhibit CYP3A drug biotransformation in the gut, some biotransformation may be decreased in other tissues as well if the gallic acid ester is absorbed into the blood stream. The decrease in biotransformation by other tissues will also increase drug bioavailability. The advantage of targeting the gallic acid ester to the gut, however, is that it allows the use of lower systemic concentrations of the gallic acid ester compared to inhibitors that target CYP3A in the liver. After oral administration of the gallic acid ester, concentrations will be highest at the luminal surface of the gut epithelia, not having been diluted by systemic fluids and the tissues of the body. Luminal concentrations that are greater compared to blood concentrations will permit preferential inhibition of CYP3A in gut instead of the liver. Thus, as orally administered gallic acid esters preferentially inhibit CYP3A in the gut, they are a particularly effective means of increasing drug bioavailability of a co-administered drug.

Coadministration of the gallic acid ester will also reduce variability of oral bioavailability. Reduction of drug biotransformation or increased drug absorption will decrease variability of oral bioavailability to some degree because the increase in bioavailability will begin to approach the theoretical maximum of 100% oral bioavailability. The increase in oral bioavailability will be generally larger in subjects with lower oral bioavailability. The result is a reduction in inter-individual and intra-individual variation. Addition of the gallic acid ester will reduce inter-individual and intra-individual variation of systemic concentrations of a drug or compound.

A Net Increase in Drug Bioavailability Due to a Decrease in the Activity of CYP3A The catalytic activities of CYP3A that are subject to inhibition include, but are not limited to, dealkylase, oxidase, and hydrolase activities. In addition to the different catalytic activities of CYP3A, different forms of CYP3A exist with a range in molecular weight (for example, from 51 kD to 54 kD, as shown in Komori et al., *J. Biochem.*, 104:912–16 (1988)).

The gallic acid esters reduce CYP3A drug biotransformation by acting as inhibitors of CYP3A activity. Possible mechanisms include competitive, non-competitive, uncompetitive, mixed or irreversible inhibition of CYP3A drug biotransformation.

Selection of Gallic Acid Ester Concentration by Reduction of CYP3A Drug Biotransformation The ability of the gallic acid ester to increase drug bioavailability of a particular drug can be estimated using in vitro and in vivo drug biotransformation measurements. In vivo measurements of drug bioavailability, such as measuring serum or blood drug concentrations over time, provide the closest measure of total drug systemic availability (bioavailability). In vitro assays of CYP3A metabolism indirectly indicate drug bioavailability because CYP3A drug metabolism affects integrated systemic drug concentrations over time. Although even a minimally measured increase is all that is required for a gallic acid ester to be useful, a preferred commercially desirable concentration of a gallic acid ester acting as a CYP3A modulator generally will increase drug bioavailability by at least 10%, preferably by at least 50%, and more preferably by at least 75% of the difference between bioavailability in its absence and complete oral bioavailability. For example, if the drug bioavailability is 40% without the gallic acid ester, then the addition of the gallic acid ester may increase bioavailability to 85%, for a 75% increase. A sufficient amount of orally administered gallic acid ester will provide integrated systemic drug concentrations over time greater than the integrated systemic drug concentrations over time in the absence of the gallic acid ester. The actual amount or concentration of the gallic acid ester to be included with a pharmaceutical compound for a particular composition or formulation will vary with the active ingredient of the compound. The amount of the gallic acid ester to be used should be optimized using the AUC methods described herein, once the components for a particular pharmaceutical composition have been decided upon. As stated above, the recommended measure for the amount of the gallic acid ester in a particular formulation is by direct comparison to the amount of drug, with a gallic acid ester:drug ratio in the range of 0.01–100:1 being preferred, 0.1–10:1 being more preferred, and 0.5–2:1 being most preferred.

Inhibition of the P450 3A class of enzymes by gallic acid esters can be studied by a variety of bioassays, several of which are set forth below.

In vitro CYP3A Assays and Increased Drug Bioavailability

Cell Assays of CYP3A Function and Increased Drug Bioavailability

Cultured cells of either hepatocytes or enterocytes or freshly prepared cells from either liver or gut can be used to determine the activity of the gallic acid ester as a CYP3A inhibitor. Various methods of gut epithelial cell isolation can be used such as the method of Watkins et al., *J. Clin. Invest.*, 80:1029–36 (1987). Cultured cells, as described in Schmiedlin-Ren et al., *Biochem. Pharmacol.*, 46:905–918 (1993), can also be used. The production of CYP3A metabolites in cells can be measured using high pressure liquid chromatograph (HPLC) methods as described in the following section for microsome assays of CYP3A activity.

Microsome Assays of CYP3A Function and Increased Bioavailability

Microsomes from liver or intestine will be used for assays of CYP3A activity. Microsomes can be prepared from liver using conventional methods as discussed in Kronbach et al., *Clin. Pharmacol. Ther.*, 43:630–5 (1988). Alternatively, microsomes can be prepared from isolated enterocytes using the method of Watkins et al., *J. Clin. Invest.*, 80:1029–1036 (1987). Microsomes from gut epithelial cells can also be prepared using calcium precipitation as described in Bonkovsky et al., *Gastroenterology*, 88:458–467 (1985). Microsomes can be incubated with drugs and the metabolites monitored as a function of time. In addition, the levels of these enzymes in tissue samples can be measured using radioimmunoassays or western blots. Additionally, the production of metabolites can be monitored using high pressure liquid chromatography systems (HPLC) and identified based on retention times. CYP3A activity can also be assayed calorimetrically measuring erythromycin demethylase activity as the production of formaldehyde as in Wrighton et al., *Mol. Pharmacol.,* 28:312–321 (1985) and Nash, *Biochem. J.,* 55:416–421 (1953).

Characteristics of Gallic Acid Esters for Reducing CYP3A Drug Metabolism

Gallic acid esters bind CYP3A quickly and inhibit while the drug is passing through the enterocyte. After the gallic acid ester reaches the heart and is distributed throughout the body the concentration of the gallic acid ester will be diluted on future passes through the liver. Concentrations of gallic acid ester used in the gut lumen are preferably selected to be effective on gut CYP3A metabolism but, due to dilution, to be less active in other tissues.

The amount of the gallic acid ester used for oral administration can be selected to achieve small intestine luminal concentrations of at least 0.1 times the $K_i$ or apparent $K_i$ for CYP3A inhibition of drug metabolism or an amount sufficient to increase systemic drug concentration levels, whichever is less. Alternatively, the amount of a gallic acid ester inhibitor of cytochrome P450 3A enzyme that will be used in a formulation can be calculated by various assays that are described in detail below. For example, one such assay measures the conversion of nifedipine to its oxidation product in an assay system containing 50–500 µg human liver microsomes, 10–100 µM nifedipine, and 1 mm NADPH in 500 µl of 0.1M sodium phosphate buffer, pH 7.4. In the practice of the method of the present invention, the initial amount of gallic acid ester is selected to provide concentrations in the lumen of the small intestine equal to or greater than concentrations that reduce the rate of conversion determined by this assay, preferably a rate reduction of at least 10%. While the actual dose of gallic acid ester in a clinical formulation might be optimized from this initial dosage depending on the results of a clinical trial, the assay as described is sufficient to establish a utilitarian dosage level.

In all of these cases, the goal in selecting a particular concentration of a gallic acid ester is increased bioavailability of the pharmaceutical compound that is being administered. Thus, a desirable goal is to provide integrated systemic concentrations over time of the pharmaceutical compound in the presence of the gallic acid ester that is greater than the integrated systemic concentrations over time of the pharmaceutical compound in the absence of the gallic acid ester by at least 10% of the difference between bioavailability in its absence and complete oral bioavailability. Preferred is attainment of "complete bioavailability," which is 100% systemic bioavailability of the administered dosage.

Screening Assay for Superior Gallic Acid Ester Formulations

In summary, the various techniques described above for screening gallic acid ester concentrations for activity levels by assaying for inhibition in the gut of a mammal of activity of a cytochrome P450 enzyme are all generally useful as methods of creating useful formulations that are most useful for increasing bioavailability of the active ingredient of a given drug in a mammal. In all of these assays, the best amounts are those that best inhibit enzymatic destruction of a tested drug in the gut of the mammal (either by direct testing in vivo or by a test that predicts such activity). When testing for inhibition of activity of a cytochrome enzyme, assays that detect inhibition of members of a cytochrome P450 3A family (for a particular mammal, particularly human) are preferred. Although in vivo assays are preferred because of the direct relationship between the measurement and gut activity, other assays, such as assays for inhibition of cytochrome P450 activity in isolated enterocytes or hepatocytes or microsomes obtained from either enterocytes or hepatocytes of the mammal in question or for inhibition of cytochrome P450 in a tissue or membrane from the gut of said mammal, are still useful as screening assays. It is possible to use enzymes from both the gut and liver interchangeably for these assays since it has been shown that CYP3A enzymes are identical in the two locations (Kolars, J. C. et al., Identification of Rifampin-Inducible P450IIIA4 (CYP3A4) in Human Small Bowel Enterocytes, *J. Clin. Investig.,* 90:1871–1878 (1992); Lown, K. S. et al., *Sequences of intestinal and hepatic cytochrome p450 3A4 cDNAs are identical. Drug Metab. Dispos.,* 26:185–187 (1998)).

Coadministration and Delivery of the Gallic Acid Ester

Coadministration of the Gallic Acid Ester and a Drug

The present invention will increase the bioavailability of a drug in systemic fluids or tissues by co-administering the gallic acid ester with a drug. "Co-administration" includes concurrent administration (administration of the gallic acid ester and drug at the same time) and time-varied administration (administration of the gallic acid ester at a time different from that of the drug), as long as both the gallic acid ester and the drug are present in the gut lumen and/or membranes during at least partially overlapping times. "Systemic fluids or tissues" refers to blood, plasma, or serum and to other body fluids or tissues in which drug measurements can be obtained.

Delivery Vehicles and Methods

Coadministration can occur with the same delivery vehicle or with different delivery vehicles. The gallic acid ester and the drug can be administered using, as examples, but not limited to, time release matrices, time release coatings, companion ions, and successive oral administrations. Alternatively, the drug and the gallic acid ester can be separately formulated with different coatings possessing different time constants for release of the gallic acid ester and the drug. The gallic acid ester can also be bound to the drug being protected, either by covalent bonding or by ionic or polar attractions.

The gallic acid ester also increases bioavailability when used with epithelia tissues other than the gut. The discussion above of the invention as used in the gut is appropriate for other types of epithelia. For example, CYP 3A enzymes are present in the skin, and a gallic acid ester can be used in transdermal formulations to increase drug bioavailability to systemic fluids and tissues. Such applications are part of the invention, since inhibition of CYP 3A enzymes by a gallic acid ester in epithelia other than the gut provides the same mechanism of action.

Formulations Having a Gallic Acid Ester

The invention is carried out in part by formulating an oral pharmaceutical composition to contain at least one gallic acid ester. This is accomplished in some embodiments by admixing a pharmaceutical compound, usually a pharmaceutical carrier, and the gallic acid ester, the gallic acid ester being present in an amount sufficient to provide integrated systemic concentrations over time of the pharmaceutical compound (as measured by AUCs greater than the integrated systemic concentrations over time of the pharmaceutical compound in the absence of the gallic acid ester) when the pharmaceutical composition is administered orally to an animal being treated. Additionally, more than one gallic acid ester may be used in the formulation. A pharmaceutical carrier is generally an inert bulk agent added to make the active ingredients easier to handle and can be solid or liquid in the usual manner as is well understood in the art. Pharmaceutical compositions produced by the process described herein are also part of the present invention.

The present invention can also be used to increase the bioavailability of the active compound of an existing oral pharmaceutical composition. When practiced in this manner, the invention is carried out by reformulating the existing composition to provide a reformulated composition by admixing the active compound with the gallic acid ester, the gallic acid ester being present in an amount sufficient to provide integrated systemic concentrations over time of the compound when administered in the reformulated composition greater than the integrated systemic concentrations over time of the compound when administered in the existing pharmaceutical composition. All of the criteria described for new formulations also apply to reformulation of old compositions. In preferred aspects of reformulations, the reformulated composition comprises all components present in the existing pharmaceutical composition plus the gallic acid ester, thus simplifying practice of the invention, although it is also possible to eliminate existing components of formulations because of the increase in bioavailability. Thus, the invention also covers reformulated compositions that contain less than all components present in the existing pharmaceutical composition plus the gallic acid ester. However, this invention does not cover already existing compositions that contain a component which increases bioavailability by mechanisms described in this specification (without knowledge of the mechanisms), should such compositions exist.

Traditional formulations can be used with the gallic acid ester. Optimal gallic acid ester concentrations can be determined by varying the amount and timing of gallic acid ester administration and monitoring bioavailability. Once the optimal gallic acid ester concentration or gallic acid ester to drug ratio is established for a particular drug, the formulation (gallic acid ester, drug, and other formulation components, if any) is tested clinically to verify the increased bioavailability. In the case of time- or sustained-release formulations, it will be preferred to establish the optimal gallic acid ester concentration using such formulations from the start of the bioavailability experiments.

Several gallic acid esters have been used as antioxidants under many different circumstances, including as part of a pharmaceutical composition or formulation. Their use has been limited to preventing decomposition of the materials in the formulation, rather than for a physiological effect. As antioxidants, gallic acid esters are used in small quantities, and such materials are not likely to approach even the outer limits of the present invention as defined by the specification and claims. In particular, preferred formulations of the invention contain at least 1% by weight gallic acid ester relative to the total weight of the formulation (including the capsule, if present), more preferably at least 2%, even more preferably at least 5%. For example, propyl gallate, when used as an antioxidant, is used in an amount that is less than 0.1% of the materials being protected or preserved. Other gallic acid esters, for example octyl gallate or lauryl gallate, are used as antioxidants at equivalent or lower levels. In considering these percentages, it should be recalled that these are percentages of the formulation in which the active ingredient is being presented, not percentages by weight or volume as concentrations in the medium in which the pharmaceutical composition will become dissolved or suspended after ingestion of the formulation. Furthermore, the gallic acid ester may be used in capsules (either hard or soft standard pharmaceutical gel capsules, for example).

The invention now being generally described, the same will be better understood by reference to the following detailed example, which is offered for illustration only and is not to be considered limiting of the invention unless otherwise specified.

EXAMPLES

Example 1

Inhibition of Drug Degradation by Gallic Acid Esters

The known CYP3A substrate nifedipine (Gonzalez, F. J., et al., Human P450PCN1: sequence, chromosome localization, and direct evidence through cDNA expression that P450PCN1 is nifedipine oxidase, *DNA*, 2:79–86 (1988)) was used as a test substrate for evaluating the potential of various gallic acid esters to inhibit CYP3A metabolism in a human liver microsome study.

To prepare the microsomes, human liver pieces were perfused with 1.15% potassium chloride then homogenized in 0.1 mM Tris-acetate, pH 7.4, containing 1 mM EDTA and 20 mM BHT. Microsomal pellets were prepared from the homogenate using standard differential centrifugation procedures (Guengerich, Analysis and characterization of enzymes in *Principles and Methods of Toxicology*, A. W. Hayes (ed.), Raven Press, New York. pp. 777–814 (1989)) and were stored at −80° C. in Tris-acetate buffer, pH 7.4, containing 20% w/v glycerol. Microsomes were diluted in 100 mM potassium phosphate buffer, pH 7.4, for use in metabolic incubations. Microsomal protein and CYP content of the human liver microsomes were determined using methods of Bradford (Bradford, M. M. A rapid and sensitive method for the quantitation of microgram quantities of protein utilizing the principles of protein-dye binding. *Anal. Biochem.* 72:248–254 (1976)) and Omura and Sato (Omura, T. et. al. The carbon monoxide-binding pigment of liver microsomes II. Solubilization, purification and properties. *J. Biol. Chem.* 239:2370–2378 (1964)), respectively.

In the experiments, 100 $\mu$M nifedipine and either 5 $\mu$l of a solution of one of the gallic acid esters (at a concentration indicated in Table 1) or 5 $\mu$l of solvent alone (control) were preincubated along with 0.1 mg/ml of the human liver microsomal proteins and 1 mM diethylenetriarninepentaacetic acid (DETAPAC) in 100 mM phosphate buffer, pH 7.4, for 5 minutes at 37°0 C. Metabolic reactions were started by addition of reduced $\beta$-nicotinamide adenine dinucleotide phosphate (NADPH) to give a final concentration of 1 mM and a final volume of 0.5 ml. Metabolic reactions were stopped after 3 minutes by vortex mixing with 0.2 ml of an extraction solvent of (94:6) acetonitrile:glacial acetic acid. Protein was precipitated by centrifugation (3000 rpm×10 minutes) and supernatants were analyzed for nifedipine and its oxidation product 2,6-dimethyl-4-(2-nitrophenyl)-3,5-pyridinedicarboxylic acid dimethyl ester by High Performance Liquid Chromatography (HPLC).

All experiments were conducted in triplicate and compared to incubations carried out without NADPH or without substrate. The data are the mean±standard deviation of three measurements.

The results, shown in Table 1, indicate that nifedipine oxidation rates in the presence of all gallic acid esters tested at the indicated concentrations were significantly different from the control ($P<0.05$) using ANOVA with Dunnett's post hoc comparison.

TABLE 1

Inhibition of CYP3A-Mediated Metabolism in
Human Liver Microsomes by Gallic Acid Esters

| Inhibitor[a] | Conc. ($\mu$M) | Relative Nifedipine Oxidation Rate (± S.D.) | Comment |
|---|---|---|---|
| Control | — | 100 (3) | |
| Methyl gallate | 100 | 53 (2) | |
| | 500 | 16.0 (0.1) | |
| Propyl gallate | 50 | 59 (2) | Non-competitive inhibitor of |
| | 100 | 34 (1) | nifedipine metabolism $K_i$ = |
| | 500 | 6.1 (0.1) | 64 ± 2 $\mu$M (mean ± S.E. of estimate; $r^2$ = 0.999)[b] |
| Octyl gallate | 10 | 44 (2) | Non-competitive inhibitor of |
| | 25 | 17.5 (0.5) | nifedipine metabolism $K_i$ = |
| | 50 | 4.9 (0.6) | 5.2 ± 0.2 $\mu$M (mean ± S.E. of |
| | 100 | 1.1 (0.3) | estimate; $r^2$ = 0.996)[b] |
| Lauryl gallate | 10 | 61 (1) | |
| (Dodecyl gallate) | 25 | 31 (3) | |
| | 50 | 12.6 (0.1) | |
| | 100 | 6.4 (0.5) | |

[a]Substrate and inhibitor were dissolved in acetonitrile except for lauryl gallate which required methanol as vehicle.
[b]Inhibition constant $K_i$ determinations utilized 10, 20, 50 and 100 $\mu$M nifedipine substrate concentrations and experiments were run in duplicate. $K_i$ values were determined by regression analysis of rate data using SigmaPlot V4.OS software (SPSS Inc., San Rafael, California).

The various gallic acid esters, at all tested concentrations, served as effective inhibitors of CYP3A-mediated metabolism. Octyl gallate proved to be an especially good inhibitor of the metabolism at relatively low concentrations. The usefulness of gallic acid esters to increase bioavailability of pharmaceutical compounds given to patients by coadministration of the gallic acid ester with the pharmaceutical compound is thus self-evident.

Example 2

Inhibition of Drug Degradation by Propyl Gallate

The ability of propyl gallate at various concentrations to inhibit metabolism for three representative drugs through inhibition of the cytochrome P450 mechanism was tested. Human liver microsomes were prepared and each of three drugs, amiodarone, buspirone, or nifedipine, were incubated with the microsomes in the presence of propyl gallate or a known inhibitor of CYP3A metabolism. Metabolism in the presence of propyl gallate or known CYP3A inhibitor was compared to a control treated only with the solvent in which the inhibitor was dissolved.

Inhibition of metabolism of the known CYP3A substrates amiodarone (Fabre, G., et al., Evidence for CYP3A-mediated N-deethylation of amiodarone in human liver microsomal fractions, *Drug Metab. Dispos.*, 21:978–985 (1993), Triver, J. M., et al., Amiodarone N-deethylation in human liver microsomes: involvement of cytochrome P450 3A enzymes (first report), *Life Sci.*, 52:PL91–96 (1993)), nifedipine (Gonzalez, F. J., et al., Human P45OPCN1: sequence, chromosome localization, and direct evidence through cDNA expression that P45OPCN1 is nifedipine oxidase, *DNA*, 7:79–86 (1988)), and buspirone (Kivisto K. T. et al. Plasma buspirone concentrations are greatly increased by erythromycin and itraconazole. *Clin. Pharmacol. Ther.* 62: 348–54 (1997); Lilja J. J. Grapefruitjuice substantially increases plasma concentrations of buspirone. *Clin. Pharmacol. Ther.* 64: 655–60 (1998)) by human liver microsomes was tested. The microsomes were prepared as in Example 1.

The amiodarone was present in a concentration of 100 $\mu$M, the buspirone was in a concentration of 25 $\mu$M, and the nifedipine was present in a concentration of 25 $\mu$M. The propyl gallate was tested with each of these drugs at concentrations of 25, 50, and 100 $\mu$M. Other inhibitors of CYP3A metabolism were utilized at known inhibition concentrations, i.e. ketoconazole at 1 $\mu$M, cyclosporine at 25 $\mu$M, and diltiazem, erythromycin, and verapamil at 100 $\mu$M.

The drug and optionally the inhibitor were preincubated with the microsomes at 1 nmol CYP/ml and 1 mM DETAPAC in 100 mM phosphate buffer, pH 7.4 for 5 minutes at 37° C. After the preincubation, metabolic reactions were started by the addition of 1 mM NADPH. Samples were taken at 1, 2, and 3 minutes after the start of the reaction and analyzed by HPLC. Disappearance of substrate and/or formation of metabolite were quantitated by comparison to standard curves.

The results are presented in Table 2. The metabolism rates (nmol/ml/min) are the mean±standard deviation of three measurements. Also shown in Table 2 are the metabolism rates expressed as a percentage of the control for each drug. These numbers are presented in parentheses.

TABLE 2

Inhibition of CYP3A-Mediated Metabolism in
Human Liver Microsomes by Propyl Gallate

| | | Mean ± SD Metabolism rate (% control) | | |
|---|---|---|---|---|
| Inhibitor | $\mu$M | Amiodarone[a] | Buspirone[b] | Nifedipine[c] |
| Control | | 1.92 ± 0.08 (100) | 5.37 ± 0.56 (100) | 4.36 ± 0.17 (100) |
| Propyl Gallate | 25 | 0.94 ± 0.02 (49) | 3.49 ± 0.49 (65) | 3.57 ± 0.29 (82) |
| | 50 | 0.55 ± 0.02 (28) | 2.25 ± 0.25 (42) | 2.35 ± 0.10 (54) |
| | 100 | 0.32 ± 0.03 (17) | 1.55 ± 0.23 (29) | 1.43 ± 0.04 (33) |
| Ketoconazole | 1 | 0.79 ± 0.004 (4) | 1.47 ± 0.39 (28) | 0.48 ± 0.06 (11) |
| Cyclosporine | 25 | 0.32 ± 0.03 (17) | 2.21 ± 0.38 (41) | 1.05 ± 0.02 (24) |
| Diltiazem | 100 | 1.06 ± 0.02 (55) | 2.80 ± 0.18 (52) | 3.74 ± 0.16 (86) |
| Erythromycin | 100 | 0.84 ± 0.07 (44) | 3.59 ± 0.46 (67) | 2.67 ± 0.11 (61) |
| Verapamil | 100 | 0.81 ± 0.04 (42) | 2.34 ± 0.46 (44) | 3.00 ± 0.05 (69) |

[a]Formation rate of N-desethylamiodarone metabolite (nmol/ml/min)
[b]Buspirone disappearance (nmol/ml/min)
[c]Formation of nifedipine oxidation product 2,6-dimethyl-4-(2-nitrophenyl)-3,5-pyridinedicarboxylic acid, dimethyl ester (nmol/ml/min)

As evidenced above, propyl gallate at all tested concentrations and against each drug, served as an effective inhibitor of CYP3A-mediated metabolism. Greater inhibition of the metabolism occurred with increasing concentrations of propyl gallate. Propyl gallate also compared favorably with the known CYP3A inhibitors tested. Specifically, propyl gallate was found to be better at inhibiting drug metabolism than the established CYP3A inhibitors diltiazem, erythromycin, and verapamil. This demonstrates the utility of propyl gallate to increase bioavailability of compounds by coadministration of propyl gallate with a pharmaceutical compound.

All publications and patent applications mentioned in this specification are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

We claim:

1. A method for increasing bioavailability of an orally administered pharmaceutical compound, the method comprising:
    orally coadministering (1) the pharmaceutical compound to a mammal in need of treatment with the compound and (2) a gallic acid ester in an amount of the gallic acid ester sufficient to provide bioavailability of the compound in the presence of the gallic acid ester greater than bioavailability of the compound in the absence of the gallic acid ester.

2. The method of claim 1, wherein the gallic acid ester has the formula

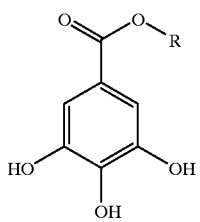

wherein R is a substituted or unsubstituted alkyl, alkenyl, alkynyl, aryl, benzyl, phenyl, alicyclic or heterocyclic group.

3. The method of claim 2, wherein R is a substituted or unsubstituted alkyl, alkenyl or alkynyl group.

4. The method of claim 3, wherein R is a $C_1$–$C_{22}$ alkyl group or a $C_2$–$C_{22}$ alkenyl group.

5. The method of claim 4, wherein R is a $C_1$–$C_{12}$ alkyl group.

6. The method of claim 5, wherein R is selected from the group consisting of a methyl group, a propyl group, an octyl group, and a lauryl group.

7. The method of claim 4, wherein R is a $C_2$–$C_{18}$ alkenyl group.

8. The method of claim 4, wherein R is selected from the group consisting of a methyl group, a propyl group, an octyl group, a lauryl group, a cis-9-hexadecenyl group, a cis-9-octadecenyl group, a cis,cis-9,12-octadecadienyl group, a trans,tans-9,12-octadecadienyl group, a cis,cis,cis-9,12,15-octadecatienyl group, a trans,trans,trans-9,12,15-octadecatrienyl group, a cis,cis,cis-6,9,12-octadecatrienyl group, a trans-9-octadecenyl group, and a trans-9-hexadecenyl group.

9. The method of claim 1, wherein the gallic acid ester is coadministered in a range of 0.01 to 100 units of the gallic acid ester per 1 unit of the pharmaceutical compound.

10. The method of claim 9, wherein the gallic acid ester is coadministered in a range of 0.1 to 10 units of the gallic acid ester per 1 unit of the pharmaceutical compound.

11. The method of claim 10, wherein the gallic acid ester is coadministered in a range of 0.5 to 2 units of the gallic acid ester per 1 unit of the pharmaceutical compound.

12. The method of claim 1, wherein two or more gallic acid esters are coadministered with the pharmaceutical compound, the gallic acid esters including at least two of octyl gallate, propyl gallate, lauryl gallate, and methyl gallate.

13. The method of claim 1, wherein the pharmaceutical compound is hydrophobic.

14. The method of claim 1, wherein the amount is sufficient to produce a concentration of the gallic acid ester in the lumen of the gut of the mammal of at least 0.1 times a $K_i$ or apparent $K_i$ of CYP3A inhibition of the compound.

15. The method of claim 1, wherein bioavailability of the compound in the presence of the gallic acid ester is greater than bioavailability of the compound in the absence of the gallic acid ester by at least 10% of the difference between bioavailability in the absence of the gallic acid ester and complete oral bioavailability.

16. The method of claim 15, wherein bioavailability of the compound in the presence of the gallic acid ester is greater than bioavailability of the compound in the absence of the gallic acid ester by at least 50% of the difference between bioavailability in the absence of the gallic acid ester and complete oral bioavailability.

17. The method of claim 16, wherein bioavailability of the compound in the presence of the gallic acid ester is greater than bioavailability of the compound in the absence of the gallic acid ester by at least 75% of the difference between bioavailability in the absence of the gallic acid ester and complete oral bioavailability.

18. The method of claim 1, wherein the gallic acid ester shows an inhibition of at least 20% when the gallic acid ester and the compound are present in a 1:1 gallic acid ester:compound ratio.

19. The method of claim 1, wherein the pharmaceutical compound comprises an acetanilide, aminoacridine, aminoquinoline, anilide, anthracycline antibiotic, antiestrogen, benzazepine, benzhydryl compound, benzodiazapine, benzofuran, cannabinoid, cephalosporine, colchicine, cyclic peptide, dibenzazepine, digitalis glycoside, dihydropyridine, epiphodophyllotoxin, ergeline, ergot alkaloid, imidazole, isoquinoline, macrolide, naphthalene, nitrogen mustard, opioid, oxazine, oxazole, paclitaxel, phenothiazine, phenylalkylamine, phenylpiperidine, piperazine, piperidine, polycyclic aromatic hydrocarbon, pyridine, pyridone, pyrimidine, pyrrolidine, pyrrolidinone, quinazoline, quinoline, quinone, rauwolfia alkaloid, retinoid, salicylate, steroid, stilbene, sulfone, sulfonylurea, triazole, tropane, or vinca alkaloid.

20. The method of claim 1, wherein the gallic acid ester is present as a counter ion of the pharmaceutical compound.

21. The method of claim 1, wherein the gallic acid ester is covalently bound to the pharmaceutical compound.

22. A method of formulating an oral pharmaceutical composition, the method comprising:
    admixing a pharmaceutical compound, a pharmaceutical carrier, and a gallic acid ester, the gallic acid ester being present in sufficient amount to provide bioavailability of the pharmaceutical compound in the presence of the gallic acid ester greater than the bioavailability of the pharmaceutical compound in the absence of the gallic acid ester when the pharmaceutical composition is administered orally to a mammal.

23. The method of claim 22, wherein the gallic acid ester has the formula

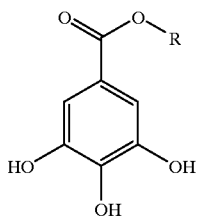

wherein R is a substituted or unsubstituted alkyl, alkenyl, alkynyl, aryl, benzyl, phenyl, alicyclic or heterocyclic group.

24. The method of claim 23, wherein R is a substituted or unsubstituted alkyl, alkenyl or alkynyl group.

25. The method of claim 24, wherein R is a $C_1$–$C_{22}$ alkyl group or a $C_2$–$C_{22}$ alkenyl group.

26. The method of claim 25, wherein R is a $C_1$–$C_{12}$ alkyl group.

27. The method of claim 26, wherein R is selected from the group consisting of a methyl group, a propyl group, an octyl group, and a lauryl group.

28. The method of claim 25, wherein R is a $C_2$–$C_{18}$ alkenyl group.

29. The method of claim 25, wherein R is selected from the group consisting of a methyl group, a propyl group, an octyl group, a lauryl group, a cis-9-hexadecenyl group, a cis-9-octadecenyl group, a cis,cis-9,12-octadecadienyl group, a trans,trans-9,12-octadecadienyl group, a cis,cis,cis-9,12,15-octadecatrienyl group, a trans,trans,trans-9,12,15-octadecatrienyl group, a cis,cis,cis-6,9,12-octadecatrienyl group, a trans-9-octadecenyl group, and a trans-9-hexadecenyl group.

30. The method of claim 22, wherein the gallic acid ester is present in a range of 0.01 to 100 units of the gallic acid ester per 1 unit of the pharmaceutical compound.

31. The method of claim 30, wherein the gallic acid ester is present in a range of 0.5 to 2 units of the gallic acid ester per 1 unit of the pharmaceutical compound.

32. The method of claim 22, wherein the gallic acid ester is present in an amount sufficient to produce a concentration of the gallic acid ester in the lumen of the gut of the mammal of at least 0.1 times a $K_i$ or apparent $K_i$ of CYP3A inhibition of the compound.

33. The method of claim 22, wherein bioavailability of the compound in the presence of the gallic acid ester is greater than bioavailability of the compound in the absence of the gallic acid ester by at least 10% of the difference between bioavailability in the absence of the gallic acid ester and complete oral bioavailability.

34. The method of claim 22, wherein the gallic acid ester is present in an amount sufficient to provide at least 1% by weight of the gallic acid ester relative to the total weight of the pharmaceutical composition.

35. The method of claim 22, wherein two or more gallic acid esters are admixed with the pharmaceutical compound and the pharmaceutical carrier, the gallic acid esters including at least two of octyl gallate, propyl gallate, lauryl gallate, and methyl gallate.

36. The method of claim 22, wherein the gallic acid ester is present as a counter ion of the pharmaceutical compound.

37. The method of claim 22, wherein the gallic acid ester is covalently bound to the pharmaceutical compound.

38. The method of claim 22, wherein the pharmaceutical compound comprises an acetanilide, aminoacridine, aminoquinoline, anilide, anthracycline antibiotic, antiestrogen, benzazepine, benzhydryl compound, benzodiazapine, benzofuran, cannabinoid, cephalosporine, colchicine, cyclic peptide, dibenzazepine, digitalis glycoside, dihydropyridine, epiphodophyllotoxin, ergeline, ergot alkaloid, imidazole, isoquinoline, macrolide, naphthalene, nitrogen mustard, opioid, oxazine, oxazole, paclitaxel, phenothiazine, phenylalkylamine, phenylpiperidine, piperazine, piperidine, polycyclic aromatic hydrocarbon, pyridine, pyridone, pyrimidine, pyrrolidine, pyrrolidinone, quinazoline, quinoline, quinone, rauwolfia alkaloid, retinoid, salicylate, steroid, stilbene, sulfone, sulfonylurea, triazole, tropane, or vinca alkaloid.

39. A pharmaceutical composition produced by the process of claim 22.

40. The composition of claim 39, wherein the gallic acid ester is present in an amount sufficient to provide at least 1% by weight of the gallic acid ester relative to the total weight of the pharmaceutical composition.

41. A method of increasing bioavailability of the active compound of an existing oral pharmaceutical composition, the method comprising:

reformulating the existing composition to provide a reformulated oral composition by admixing the active compound with a gallic acid ester, the gallic acid ester being present in sufficient amount to provide bioavailability of the active compound when administered in the reformulated composition greater than said bioavailability of the active compound when administered in the existing pharmaceutical composition.

42. The method of claim 41, wherein the gallic acid ester has the formula

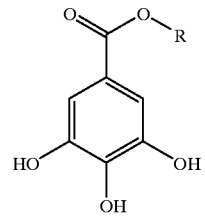

wherein R is a substituted or unsubstituted alkyl, alkenyl, alkynyl, aryl, phenyl, benzyl, alicyclic or heterocyclic group.

43. The method of claim 42, wherein R is a substituted or unsubstituted alkyl, alkenyl or alkynyl group.

44. The method of claim 43, wherein R is a $C_1$–$C_{22}$ alkyl group or a $C_2$–$C_{22}$ alkenyl group.

45. The method of claim 44, wherein R is a $C_1$–$C_{12}$ alkyl group.

46. The method of claim 45, wherein R is selected from the group consisting of a methyl group, a propyl group, an octyl group, and a lauryl group.

47. The method of claim 44, wherein R is a $C_2$–$C_{18}$ alkenyl group.

48. The method of claim 44, wherein R is selected from the group consisting of a methyl group, a propyl group, an octyl group, a lauryl group, a cis-9-hexadecenyl group, a cis-9-octadecenyl group, a cis,cis-9,12-octadecadienyl group, a trans,trans-9,12-octadecadienyl group, a cis,cis,cis-9,12,15-octadecatrienyl group, a trans,trans,trans-9,12,15- octadecatrienyl group, a cis,cis,cis-6,9,12-octadecatrienyl group, a trans-9-octadecenyl group, and a trans-9-hexadecenyl group.

49. The method of claim 41, wherein the gallic acid ester is present in a range of 0.01 to 100 units of the gallic acid ester per 1 unit of the pharmaceutical compound.

50. The method of claim 49, wherein the gallic acid ester is present in a range of 0.5 to 2 units of the gallic acid ester per 1 unit of the pharmaceutical compound.

51. The method of claim 41, wherein the reformulated oral composition comprises all components present in the existing pharmaceutical composition plus the gallic acid ester.

52. The method of claim 41, wherein the reformulated oral composition contains less than all components present in the existing pharmaceutical composition plus the gallic acid ester.

53. The method of claim 41, wherein two or more gallic acid esters are admixed with the active compound, the gallic acid esters including at least two of octyl gallate, propyl gallate, lauryl gallate, and methyl gallate.

54. A reformulated oral pharmaceutical composition produced by the process of claim 41.

* * * * *